United States Patent [19]
Saur

[11] Patent Number: 5,597,464
[45] Date of Patent: Jan. 28, 1997

[54] FLOW-THROUGH CELL WITH A HANGING MERCURY DROP ELECTRODE

[76] Inventor: Dietrich Saur, Rilkeallee 39A, D-55127 Mainz, Germany

[21] Appl. No.: 310,956

[22] Filed: Sep. 21, 1994

[30] Foreign Application Priority Data

Sep. 24, 1993 [DE] Germany .................. 9314456 U

[51] Int. Cl.⁶ ............................................. G01N 27/26
[52] U.S. Cl. ..................... 204/409; 204/412; 204/413
[58] Field of Search ................... 204/409, 412, 204/413

[56] References Cited

U.S. PATENT DOCUMENTS 4,220,515  9/1980  de Kreuk .................. 204/413

Primary Examiner—Bruce F. Bell

[57] ABSTRACT

A flow-through cell has a working electrode, an auxiliary electrode, a reference electrode, and a channel. The working electrode is a mercury drop electrode. The channel has a cross-sectional area of less than 1 mm² in the region of the working electrode. The mercury drop is situated in the channel.

21 Claims, 3 Drawing Sheets

"Prior Art"

"Prior Art"

FLOW-THROUGH CELL WITH A HANGING MERCURY DROP ELECTRODE

BACKGROUND OF THE INVENTION

Quantitative determinations of cations, anions and electochemically active organic compounds can be carried out by voltammetric methods of analysis, such as for instance polarography, voltammetry, adsorption voltammetry, inverse voltammetry or chronoamperometric methods.

The analysis of a set of sample solutions can be done in a batch-like fashion or by using flow-through cells.

In the batch-type method, the sample solutions are transferred to sample vessels with a volume of about 1 to 50 ml. Subsequent analysis of the samples is carried out using a working electrode (mercury drop(ping) electrode), an auxiliary electrode and a reference electrode, all three of which are submerged into the sample solution. A disadvantage of this method and apparatus is that before refilling the sample vessels with subsequent sample solutions the sample vessels must be emptied and cleaned which requires large, additional volumes of sample solutions and is time consuming. In addition, the instrumentation for automatically changing sample solutions becomes costly and cumbersome. If inverse or adsorption voltammetry or other electrochemical methods involving enrichment of the electroactive species onto the working electrode are applied, it is necessary to stir the sample solution to obtain an effective enrichment. After the enrichment step, the stirring is stopped and the actual measurement of the electrochemically active species is performed once the sample solution has become quiescent since the measurement is based on a purely diffusion controlled process and convection currents in the sample solution interfere with the diffusion process. A disadvantage of using a large volume of sample solution is that the quiescent state is only reached several minutes after the stirring has been stopped.

Improvements are obtained if flow-through cells are used in which the sample solution flows through a narrow channel. Smaller volumes of sample solutions are required and the removal of the sample solution from the channel after analysis as well as the cleaning of the cell and subsequent refilling with the next sample solution is easily and quickly performed. Wall jet adapters (FIG. 10) do not belong to the flow-through cells and have a limited suitability, especially for inverse voltammetric methods, because of the reasons mentioned above.

W. W. Kubiak presents a review of flow-through cells with mercury drop(ping) electrodes in Electroanalysis, vol. 1, pp 379–388 (1989). Among others, a flow-through cell is described in which the channel is essentially horizontal and the mercury working electrode is placed vertically onto the channel. It is pointed out that the diameter of the channel should not be too small if a mercury dropping electrode is employed because the removal and collection of used mercury becomes a problem. With a handling mercury drop electrode this problem is less serious. In the state-of-the-art flow-through cells channel cross-sectional areas of usually 2 $mm^2$ or more are employed.

SUMMARY OF THE INVENTION

In spite of the prejudices prevailing among experts in the field good results are obtained with a channel having a cross-sectional area of less than 1 $mm^2$ in the region of the working electrode. High deposition rates are obtained and rinsing and cleaning of the channel only takes a few seconds. Therefore, deposition times and the times necessary to carry out the measurements are correspondingly faster. In addition, the sensitivities are increased substantially compared to those obtained with the usual batch cells: experiments showed that sensitivities were increased by at least a factor of five.

In contradiction to reports in the literature, excellent results are obtained with a channel having a cross-sectional area of less than 0.6 $mm^2$ in the region of the working electrode. For a mercury drop with a diameter of about 0.05 mm, which is the smallest drop size that can presently be generated by reasonable technical means, a channel cross-sectional area of about 0.01 $mm^2$ is required to achieve the improvements as described above.

In a channel that has no obstacles to the flow of the sample solution in the region of the working electrode, other than the mercury drop itself, the flow of the solution onto the working electrode is essentially laminar, without turbulence affecting the reproducibility of the measurements.

It was also found that in a channel having constrictions before and after the working electrode a volume in the channel around the working electrode can be defined which is quasi isolated from the rest of the sample solution in the channel to a greater or lesser degree, depending on the cross-sectional area of the constrictions. Since diffusion of the electroactive species from the main part of the channel into the solution between the constrictions is thus impaired, the diffusion current during the quiescent period before the measurement decreases more rapidly due to a more rapid depletion of the electroactive species in the solution between the constrictions than would be the case without the constrictions. Thus the possibility exists to remove oxygen from the solution without prior deaeration of the sample solution with an inert gas.

A further improvement is accomplished by making the cross-sectional area of the constrictions adjustable so that the flow-through cell can be adapted to suit a particular measurement. One way to achieve this is by using an elastic material which seals the working electrode onto the channel. The cross-sectional area is adjusted by applying pressure onto the elastic material by suitable means. A sensitive adjustment of the cross-sectional area is thus possible. In addition, maintenance is readily carried out on this setup.

The most favorable flow of the solution onto the surface of the mercury drop is attained by placing the capillary tube of the mercury electrode essentially vertically onto the more or less horizontally positioned channel of the flow-through cell.

By placing the auxiliary electrode in the channel upstream from the working electrode, or opposite it, and the reference electrode downstream from the working electrode, the reference electrode is outside of the electric field extending between the auxiliary electrode and the working electrode. At the same time, contamination of the sample solution by electrolyte leaking from the salt bridge of the reference electrode is avoided.

At higher sensitivities irregularities due to flow profiles increasingly interfere with the measurements. Due care must be given to the mechanical construction and machining of the channel to ensure that the exchange of sample solution is not inhibited by dead volumes, niches or surface roughness. The cost of machining must, however, not increase to the point where the flow-through cell becomes economically unattractive.

A further object of the invention is, therefore, to design the flow-through cell such that it can be economically built with an accurately and smoothly machined channel, remains leakfree, is simple to work with and allows bubblefree filling of the channel with sample solution. This object is achieved by manufacturing the flow-through cell in two or more parts from a rigid plastic material, such as for instance polymethyl methacrylate, or from a glassy material. Leakfree sealing is achieved by merely pressing the parts together without using any gaskets. The disadvantages of using gaskets, viz. unfavorable flow conditions in the channel due to ageing and deformation of the gaskets, are avoided. If the cross section of the channel is to be rectangular in form the channel is readily machined by using a slabbing or milling cutter. Subsequent refinishing of the channel is not necessary. If the cross section of the channel is made semi-circular in form more favorable flow conditions in the channel and a better solution transport to the mercury drop of the electrode are achieved than with a rectangular channel. It is only necessary to machine the channel into one of the parts of the flow-through cell by circular milling. This manufacturing method is economical and already produces a channel surface smooth enough to obtain an essentially laminar flow in the channel.

The surface of commercially available rigid plastic materials, such as for instance polymethyl methacrylate, has a very high polish, so that a very good seal is obtained by merely pressing the parts together. No gaskets are required for leakfree sealing.

The channel design giving favorable flow conditions as described above is further improved on by placing the working, auxiliary and reference electrodes onto the channel so that practically no niches or dead volumes are created. This is achieved by mounting the electrodes tangentially onto the channel.

Simple and reliable removal of the mercury drop of the working electrode is ensured by suddenly increasing the flow velocity in the channel. The mercury drop is thus knocked off the capillary tube and transported out of the channel. Integration of this method into a computerized apparatus for automatic operation is easily carried out.

BRIEF DESCRIPTION OF THE DRAWINGS

A more complete and thorough understanding of preferred embodiments of the invention may be obtained from the belowstanding discussion when taken in conjunction with the following drawings.

The same numerals are used throughout the course of the discussion below for similar or identical parts of the flow-through cell of different inventive embodiments.

DETAILED DESCRIPTION OF PREFERRED EMBODIMENTS

Figure 1:
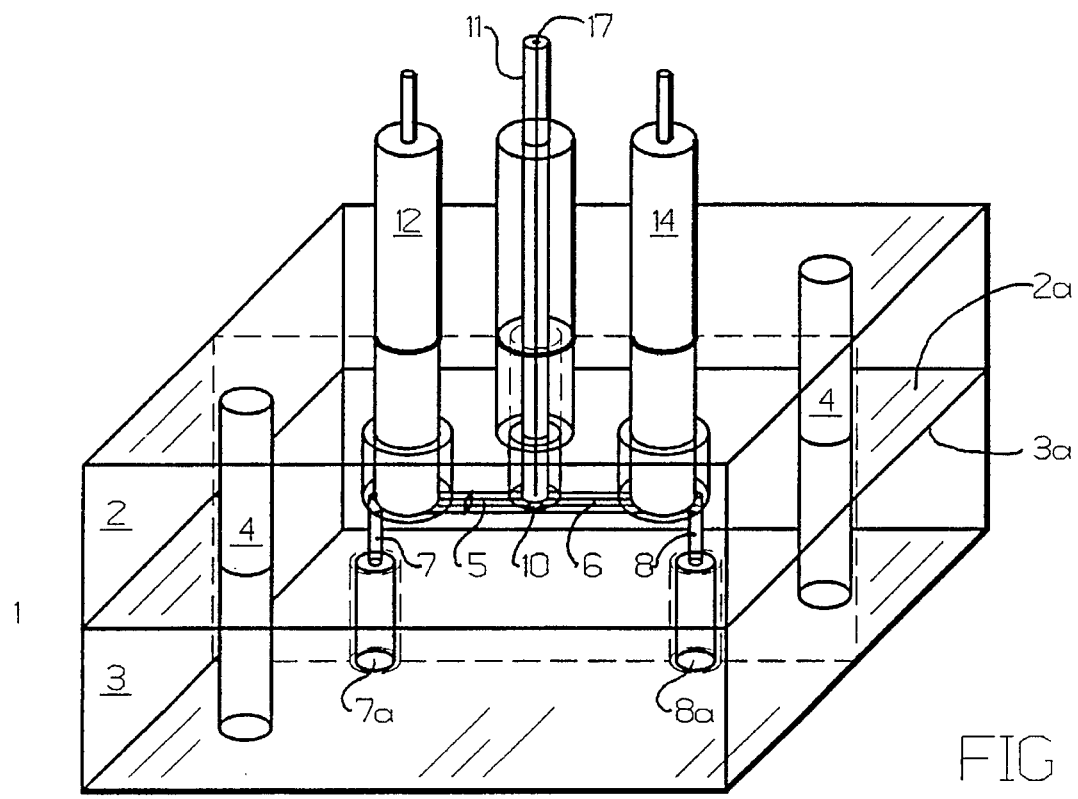
FIG. 1: Perspective drawing showing the flow-through cell as invented, with transparently drawn upper and lower cell parts.
Figure 2:
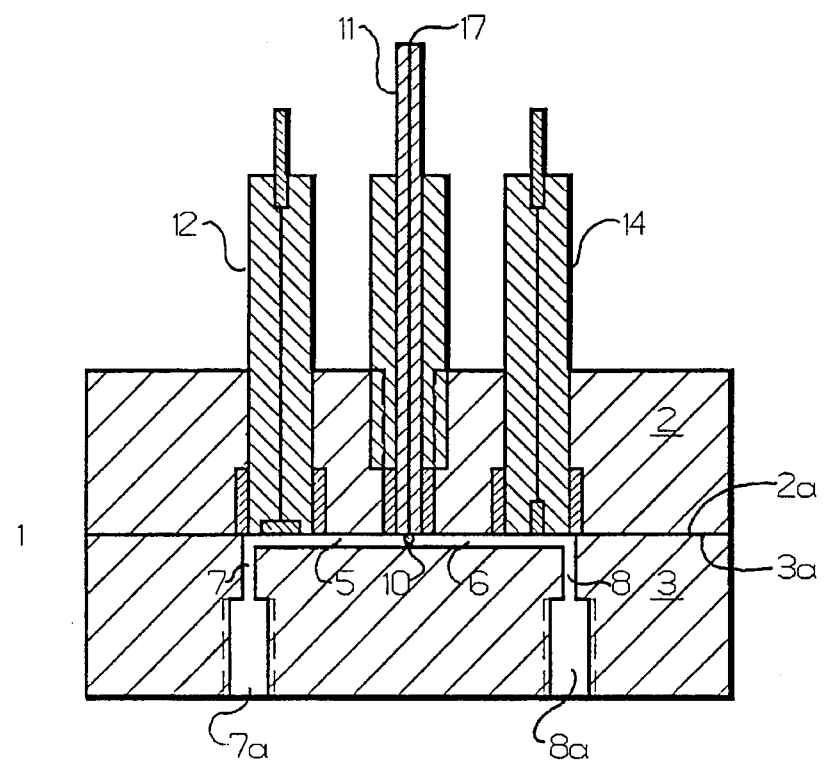
FIG. 2: Cross section of the flow-through cell shown in FIG. 1.

In FIGS. 1 to 8 the channel 6 is always shown as the groove 5 in the lower part 3 of the flow-through cell 1.

The flow-through cell 1 is comprising an upper part 2 and a lower part 3 which are pressed together along faces 2a and 3a. The upper part 2 as well as the lower part 3 are essentially rectangular in form and made of a rigid plastic material, such as for instance polymethyl methacrylate, or from a glassy material. Without gasket a durable and leakfree seal between parts 2 and 3 is obtained due to the high polish of the faces 2a and 3a pressed together. Holes 4 are drilled through both parts 2 and 3 to hold fastening bolts for pressing both parts 2 and 3 together. Alternatively, parts 2 and 3 are pressed together by holding clamps.

In the face 3a of the lower part 3 a groove 5 is machined to serve as part of the channel 6. Alternatively, the groove 5 is machined into the face 2a of part 2 or the channel is formed by two grooves 5, one of which is machined into the face 2a of part 2, the other into the face 3a of part 3. All said grooves 5 will be designated as the channel 6 from here on.

The channel 6 runs essentially vertically in the lower part 3 from the drill hole 7 up to drillhole 8. Hole 7 serves as the inlet for the sample solution into the channel 6, hole 8 as the outlet for the sample solution from the channel 6. Threads 7a and 8a are tapped part of the way into hole 7 and 8, respectively.

The delivery and removal of the sample solutions to and from the channel can be automatically performed by computerized instrumentation.

Figure 3:
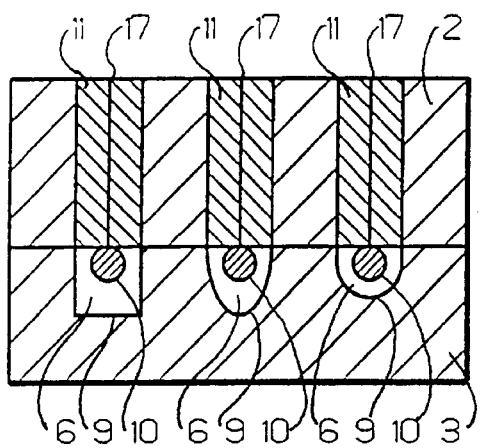
FIG. 3: Three different channel designs of the flow through cell (cross section perpendicular to the channel axis)

The cross section of the channel 6 is rectangular in form or the cross-section of the bottom 9 of the channel 6 is semi-circular in form. The mercury drop 10 of the working electrode 11 is situated essentially equidistantly from the semi-circular bottom 9, especially if the channel 6 continues upwards from the semi-circular bottom 9 with plane parallel side walls. (FIG. 3).

Part of the invention is also that the channel 6 is machined either entirely in the upper part 2 or in the lower part 3, or partially in part 2 and partially in part 3.

In the upper part 2 the auxiliary electrode 12, the working electrode 11 ond the reference electrode 14 are placed successively in the direction of the flow onto the channel 6. The auxiliary electrode 12 and the reference electrode 14 are mounted tangentially onto channel 6 so that the laminar flow in the channel 6 is not disturbed.

The auxiliary electrode 12 and the reference electrode 14 are sealed into part 2 and connected in a known fashion to a suitable measuring instrument. The working electrode 11 (a capillary tube) is perpendicular to the channel 6. The capillary tube 17 is connected to a device, not shown here, for controlled delivery of mercury. The device delivers a mercury drop 10 with a defined size. The mercury drop 10 forms the actual working electrode and is kept hanging in the channel 6 during measurement.

The mercury drop 10 is connected in a known fashion to the measuring instrument via the capillary tube 17 and the mercury supply vessel (the mercury supply vessel and the measuring instrument are not shown here). In the region of the actual working electrode, viz. the mercury drop 10, the cross-sectional area of the channel 6 is always smaller than 1 mm².

Further preferred inventive designs of the channel 6 have cross-sectional areas of less than 0.6 mm² and more than 0.01 mm².

In the design of the flow-through cell 1 most strongly favored at present the cross-sectional area of the channel 6 in the region of the mercury drop 10 is about 0.2 mm². Since the surface of the channel 6 is smoothly machined and no resistance to flow, except by the mercury drop 10 itself, exists in the channel 6, eddies or turbulences do not occur in the flowing solution.

Figure 4:
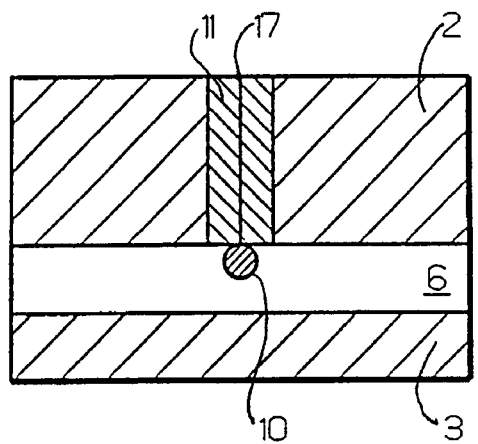
FIG. 4: Channel of the flow-through cell (cross section along the channel axis).

In the most simple design the channel 6 has the same cross-sectional area along its entire length (FIG. 4).

As a further refinement of the design, the flow-through cell 1 has devices 19 before and after the mercury drop 10 for making constrictions 18 in the channel 6. If the devices 19 are placed on both sides of the mercury drop 10 a quasi sample solution volume 22 can be defined which in essence is equal to the difference between the volume of the channel 6 between the most narrow parts and the volume of the mercury drop 10.

Figure 5:
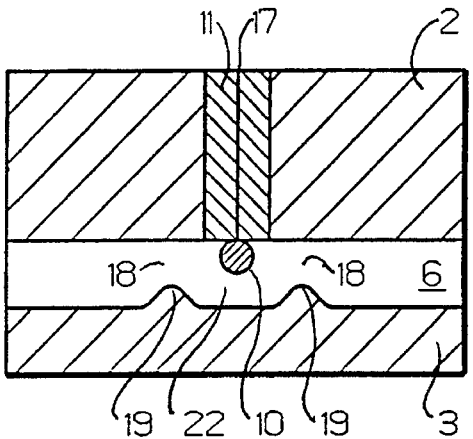
FIG. 5: Alternative design of the channel shown in FIG. 4.
Figure 6:
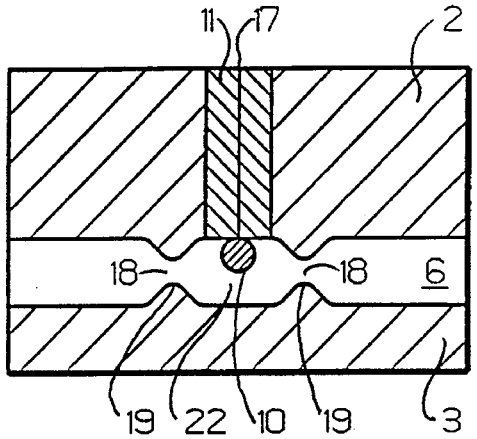
FIG. 6: Alternative design of the channel shown in FIG. 4.

The designs shown in FIG. 5 and FIG. 6 have devices 19 in the channel 6 for making constrictions 18 which cannot be altered once the channel 6 has been constructed.

Figure 7:
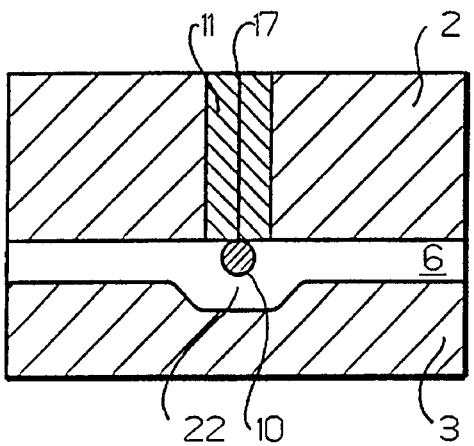
FIG. 7: Alternative design of the channel shown in FIG. 4.

A further design, the cross section of which is shown in FIG. 7, has a channel 6 with a cross-sectional area in the region of the mercury drop (10) that is larger than that of the channel 6 outside the sample volume 22.

Figure 8:
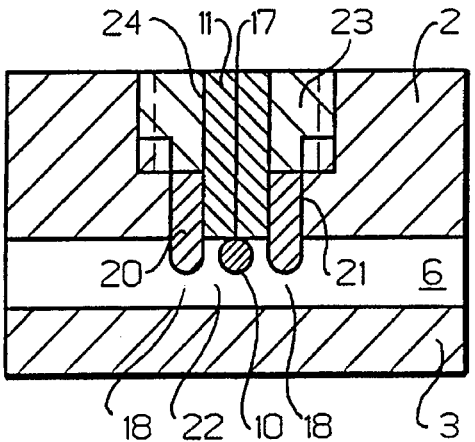
FIG. 8: Device for adjusting the cross-section area of the channel in the region of the working electrode (cross section along the channel axis).
Figure 9:
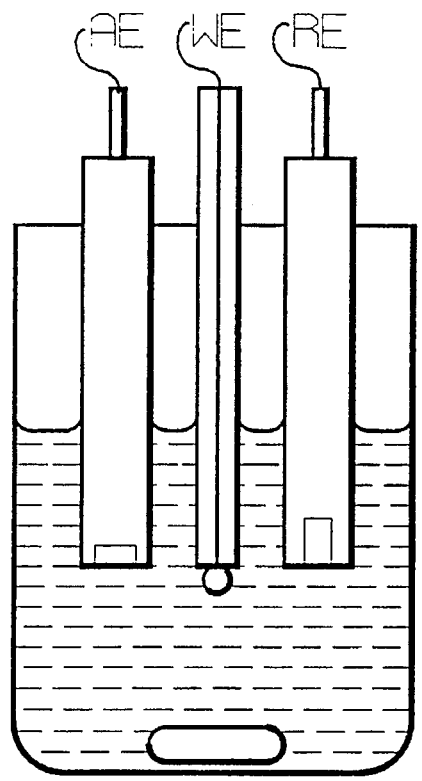
FIG. 9: Measuring vessel for batch-type operation (principle).
Figure 10:
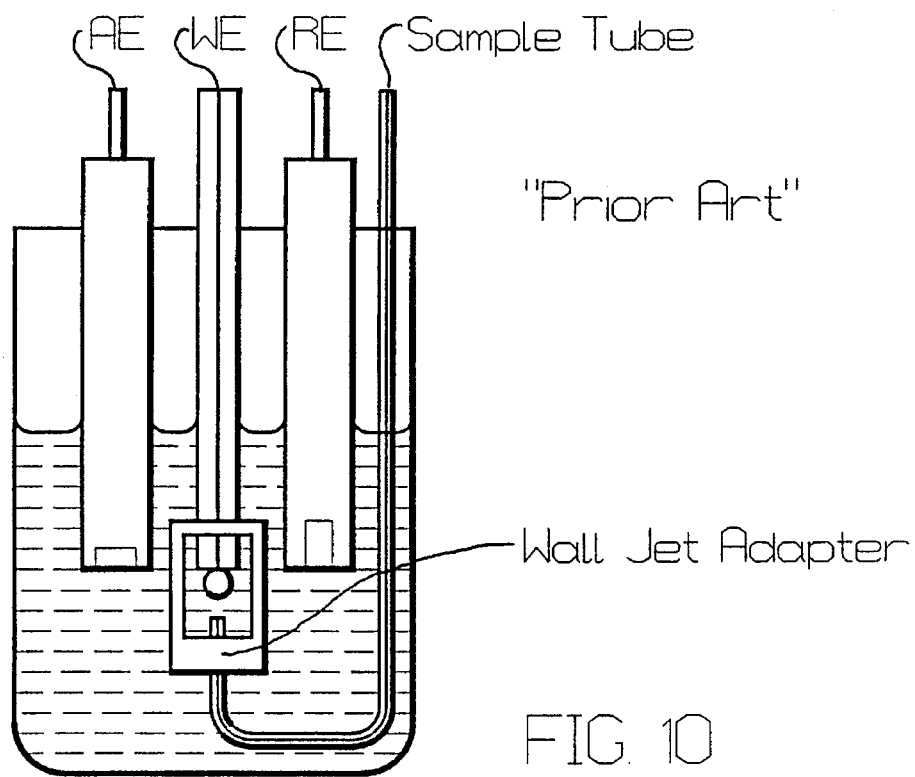
FIG. 10: Measuring vessel with wall jet adapter attached to a mercury drop electrode (principle).

A design, in which the cross-sectional areas of the constrictions 18 in the channel 6 are adjustable, is shown in FIG. 8. In this design of the flow-through cell 1 the constrictions 18 can be partially or completely closed on one side or on both sides of the mercury drop 10. Thus, influences on the sample solution in volume 22 from regions outside of the sample volume 22 or conversely, from the solution in volume 22 on regions outside the sample soution 22 are largely prevented. The device for adjusting the constrictions 18 consists of a cylindrical hole 21, the upper part of which has a larger diameter than the lower part, which is filled with an elastic sealing material 20 that encloses the capillary tube 11. The capillary tube 11 is thus sealed from the channel 6 and at the same time mechanically secured. Into the upper part of hole 21 a threaded flange is screwed which sits on the elastic material 20. The capillary tube 11 fits loosely into a cylindrical hole 24 drilled through the flange 23. If the threaded flange 23 is not inserted into the hole 21, the elastic material 20 is level and even with the wall of the channel 6 and seals off channel 6 without forming the constrictions 18. If the threaded flange 23 is inserted and screwed down onto the elastic material 20, the elastic material 20 is deformed and the cross-sectional area of the channel 6 decreases by formation of the constrictions 18. If the volume of the elastic material 20 is suitably dimensioned, the channel 6 can be constricted symmetrically, i.e. equally on both sides of the mercury drop 10, or asymmetrically, i.e. unequally on both sides of the mercury drop 10. Furthermore, if the dimensions of the elastic material 20 are properly chosen, the channel 6 can be partially or fully closed either on one side of the mercury drop 10 or on both sides.

Alternatively, but not shown here in the figures, a mechanical jack is used instead of the flange 23. The jack faces the elastic material 20 and is automatically operated by an electric, pneumatic or hydraulic device, pressing or releasing the elastic material 20 to form the constrictions 18.

In all designs described above, the flow-through cell is connected in a known fashion to a device for increasing the flow velocity in channel 6 or to a device for generating a pressure wave in the channel 6. By this means it is possible to dislodge the mercury drop 10 from the capillary tube 17 and flush the mercury drop 10 out of the channel 6 with the sample solution at increased flow velocity.

The sample solution and the mercury used are collected in a vessel attached to the outlet 8 for subsequent disposal.

What is claimed is:

1. A flow-through cell comprising a working electrode, an auxiliary electrode, a reference electrode and a channel wherein said working electrode is a mercury drop electrode, said channel has a cross-sectional area of less than 1 mm 2 in a region of said working electrode and said mercury drop is situated in said channel.

2. A flow-through cell according to claim 1 comprising a channel having a cross-sectional area of less than 0.6 mm² and more than 0.01 mm² in said region of said working electrode.

3. A flow-through cell according to claim 1 comprising a channel having a cross-sectional area of about 0.2 mm² in said region of said working electrode.

4. A flow-through cell according to claim 1 comprising a channel that substantially has no resistance to flow, other than that produced by said mercury drop itself, in said region of said working electrode.

5. A flow-through cell comprising a working electrode, an auxiliary electrode, a reference electrode, and a channel, wherein said working electrode is a mercury drop electrode, said channel has a cross-sectional area of less than 1 mm² in a region of said working electrode, said mercury drop is situated in said channel and said channel has constrictions before said mercury drop.

6. A flow-through cell according to claim 5 comprising devices for variably altering the cross-sectional area of said channel in the region of said constrictions whereby said devices are placed on one side or on both sides of said mercury drop for closing said channel partially or fully in a variable fashion.

7. A flow through cell according to claim 6 wherein said mercury drop electrode comprises a capillary tube set into a sealing and elastically deforming material that forms said constrictions.

8. A flow-through cell according to claim 5 wherein said channel has constrictions after said mercury drop.

9. A flow-through cell comprising a working electrode, an auxiliary electrode, a reference electrode, and a channel, wherein said working electrode is a mercury drop electrode, said channel has a cross-sectional area of less than 1 mm² in a region of said working electrode, said mercury drop is situated in said channel and said mercury drop electrode comprises a capillary tube, said channel extends approximately horizontally, and said mercury drop electrode is placed essentially vertically onto said approximately horizontally extending channel.

10. A flow-through cell according to claim 1 wherein said auxiliary electrode is upstream from said working electrode and said reference electrode is downstream from said working electrode.

11. A flow-through cell according to claim 1 wherein said auxiliary electrode is opposite from said working electrode and said reference electrode is downstream from said working electrode.

12. A flow-through cell comprising a working electrode, an auxiliary electrode, a reference electrode and a channel wherein said working electrode is a mercury drop electrode having a mercury drop situated in said channel, said flow-through cell is constructed from at least an upper part and a lower part, wherein said parts each has a face with a groove therein, and said channel is formed by pressing said faces together, thus obtaining a leakfree seal between said faces without a gasket between said faces.

13. A flow-through cell according to claim 12 where said groove has a bottom that is semi-circular.

14. A flow-through cell according to claim 13 wherein said semi-circular bottom has plane parallel side walls.

15. A flow-through cell according to claim 12 wherein said groove has a form selected from the group consisting of rectangular, polygonic and elliptical form.

16. A flow-through cell according to claim 12 comprising a channel having a cross-sectional area that is larger in said region of said working electrode than outside of said region of said working electrode.

17. A flow-through cell according to claim 12 comprising an upper part and a lower part formed of a material selected from the group consisting of a rigid plastic material and a vitreous material.

18. A flow-through cell according to claim 17, wherein said rigid plastic material is polymethyl methacrylate.

19. A flow-through cell according claim 12 comprising said reference electrode and said auxiliary electrode placed tangentially onto said channel.

20. A flow-through cell according to claim 12 comprising said channel connected to a device for increasing the flow velocity to dislodge said mercury drop and completely remove said dislodged mercury drop by said increased flow velocity.

21. A flow-through cell according to claim 12 comprising said channel connected to a device for generating a pressure wave to dislodge said mercury drop by said pressure increase.

* * * * *